(12) United States Patent
Monaco et al.

(10) Patent No.: US 12,075,850 B2
(45) Date of Patent: Sep. 3, 2024

(54) HYGIENIC UNDERGARMENT WITH REMOVABLE, REUSABLE, CROTCH PORTION

(71) Applicant: ME & ASSOCIATES, Yucaipa, CA (US)

(72) Inventors: Cynthia G. Monaco, Yucaipa, CA (US); Carolyn B. Evans, Lake Arrowhead, CA (US)

(73) Assignee: BELIEVE 2024 LLC, Yucaipa, CA (US)

( * ) Notice: Subject to any disclaimer, the term of this patent is extended or adjusted under 35 U.S.C. 154(b) by 0 days.

(21) Appl. No.: 16/949,423

(22) Filed: Oct. 29, 2020

(65) Prior Publication Data

US 2021/0352970 A1 Nov. 18, 2021

Related U.S. Application Data

(60) Provisional application No. 62/924,405, filed on Oct. 22, 2019.

(51) Int. Cl.
*A41B 9/00* (2006.01)
*A41B 9/12* (2006.01)

(52) U.S. Cl.
CPC .............. *A41B 9/005* (2013.01); *A41B 9/007* (2013.01); *A41B 9/12* (2013.01); *A41B 2300/32* (2013.01); *A41B 2400/70* (2013.01); *A41B 2500/00* (2013.01)

(58) Field of Classification Search
CPC ........... A41B 9/005; A41B 9/007; A41B 9/12; A41B 2300/32; A41B 2400/70
See application file for complete search history.

(56) References Cited

U.S. PATENT DOCUMENTS

| | | | | | |
|---|---|---|---|---|---|
| 2,102,359 | A | * | 12/1937 | Frieman | A61F 13/72 604/397 |
| 2,258,502 | A | * | 10/1941 | Perez | A41D 7/005 2/403 |
| 2,494,292 | A | * | 1/1950 | Frazer | A61F 13/72 604/397 |
| 2,522,010 | A | * | 9/1950 | Woodruff | A41C 3/04 D2/709 |
| 2,595,507 | A | * | 5/1952 | Beck | A61F 13/70 604/397 |
| 2,857,600 | A | * | 10/1958 | Finn | A41D 7/00 2/67 |
| 3,224,448 | A | * | 12/1965 | Diebold | A41C 1/003 2/408 |
| 3,517,666 | A | * | 6/1970 | Atlee | A41B 9/02 2/403 |
| 3,852,828 | A | * | 12/1974 | Silverstein | A41B 9/04 2/401 |
| 4,022,212 | A | * | 5/1977 | Lovison | A61F 13/70 604/391 |
| 4,280,230 | A | * | 7/1981 | LaFleur | A61F 13/70 2/408 |
| 4,421,512 | A | * | 12/1983 | Papajohn | A61F 13/76 604/396 |

(Continued)

*Primary Examiner* — Richale L Quinn
(74) *Attorney, Agent, or Firm* — James Juo

(57) ABSTRACT

A hygienic undergarment including a removeable crotch portion. The removeable crotch portion may include a pocket configured to receive an absorbent pad or other absorbable material.

20 Claims, 2 Drawing Sheets

(56) References Cited

U.S. PATENT DOCUMENTS

| | | | | |
|---|---|---|---|---|
| 4,597,110 | A * | 7/1986 | Smith, Sr. | A41B 9/007 2/408 |
| 4,675,918 | A * | 6/1987 | O'Brien | A41B 9/007 2/919 |
| 4,835,795 | A * | 6/1989 | Lonon | A41B 9/08 2/408 |
| 5,241,710 | A * | 9/1993 | Lockhart | A61F 13/74 2/400 |
| 5,711,034 | A * | 1/1998 | Cillik | A61F 13/74 604/398 |
| 5,930,838 | A * | 8/1999 | Carter-Scott-Pomije | A41D 1/06 2/408 |
| 6,412,119 | B1 * | 7/2002 | Robles | A41B 9/026 2/400 |
| 7,895,676 | B2 * | 3/2011 | Clark | A41B 9/02 2/403 |
| 9,003,571 | B1 * | 4/2015 | Lewis-Williams | A41B 9/04 2/400 |
| 9,750,287 | B2 * | 9/2017 | Cohen Larren | A41C 1/00 |
| 10,694,788 | B2 * | 6/2020 | Profeta | A41B 17/00 |
| 2006/0277649 | A1 * | 12/2006 | Smith | A41B 11/006 2/69 |
| 2008/0015538 | A1 * | 1/2008 | Deerin | A61F 13/505 604/397 |
| 2009/0118574 | A1 * | 5/2009 | Stephenson | A41B 9/04 600/38 |
| 2010/0230459 | A1 * | 9/2010 | Barbier | A45C 11/00 224/660 |
| 2014/0378936 | A1 * | 12/2014 | Coates | A61F 13/15268 604/396 |
| 2016/0338881 | A1 * | 11/2016 | Hyppolite | A61F 13/15268 |
| 2020/0000155 | A1 * | 1/2020 | Etienne | A61F 13/505 |
| 2021/0030605 | A1 * | 2/2021 | Kajanthan | A61F 13/4755 |
| 2021/0100698 | A1 * | 4/2021 | Langdon | A61F 13/496 |

* cited by examiner

HYGIENIC UNDERGARMENT WITH REMOVABLE, REUSABLE, CROTCH PORTION

FIELD OF INVENTION

This disclosure relates to women's undergarments designed to enhance the hygienic wearability of the undergarment. Specifically, the disclosure is directed to an undergarment having a crotch portion that is removable for cleaning and that can be reused.

BACKGROUND

It is estimated that million North American women suffer urinary incontinence with severity ranging from partial to complete loss of bladder control. They may experience varying degrees of urine losses, and the incontinence may change over time. For example, some women may leak a little when they laugh or cough, while others with heavy incontinence may experiencing continuous leakage.

Incontinence is not an inevitable part of aging, and it is not a disease. Unfortunately, a women's anatomy contributes to an increase likelihood of contracting various urinary or vaginal infections. The under garments worn by a woman can be a significant contributor to the urinary tract and vaginal problems described above. Unclean and soiled undergarments can contribute to these problems. Keeping their undergarments clean is one of the important preventive care factors for women's hygiene and health as a clean undergarment helps avoid maceration of her skin and bacterial overgrowth leading to urinary or vaginal infections.

Prior art garments designed to help women with incontinence are generally either relatively inexpensive and disposable, or more expensive and reusable. The reusable garments typically include a moisture absorbing pad or the like combined with an overlying moisture barrier. The moisture barrier is designed to prevent movement of moisture through the moisture absorbing pad to the outside of the garment. The prior art pads may be either disposable or reusable. When washing these pads for reuse, it is difficult to fully clean the pad due to the restricted flow of water through the pad caused by the moisture barrier. An even greater problem is the inability to efficiently and effectively dry the pad after washing. Thus, while an advantage of these pads lies in the repeated reuse ability, the considerable time and inconvenience in laundering generally outweighs the ultimate cost savings.

Additionally, the prior art garments described above are typically relatively unattractive and bulky, especially if they include large absorbent pads or diaper-like materials. Even when a garment is designed to allow the replacement of the absorbent pad or material, the interior of the moisture barrier may remain moist, and contaminate the new pad, or may leak moisture onto the skin when the pad is replaced. When this occurs, the entire undergarment will need to be replaced.

Another method of addressing the above problems has been to fully in-case an undergarment in a material that is moisture impermeable. This approach is undesirable because the retention of moisture in the absorbent garment can lead to skin and urinary tract problems. Furthermore, if a person experiences incontinence while wearing such a garment, the only way to address the moisture problem is to replace the soiled garment with a new garment.

What has been needed, not available before, is an undergarment that is attractive and easy to wear, yet still allows a portion of the undergarment to be easily removed for replacement without removing the entire undergarment from the body. Such a removeable portion of the undergarment may also include a pocket holding an absorbent material that can be removed from the pocket and replaced with a dry absorbent material or pad. The removable portion may then be reattached to the rest of the undergarment without removing the entire undergarment from the body. The present invention satisfies these and other needs.

SUMMARY OF THE INVENTION

In its most general aspect, the invention includes an undergarment having a removeable crotch portion that may be fitted with an absorbent material disposed to absorb any fluids leaking from a user's body. The removeable crotch portion may include a pocket or cavity sized and arranged to receive a pad or other absorbable material. The removeable crotch portion may be fastened to front and rear panels of the undergarment in a manner to removably maintain the crotch portion in place during use, but allowing the removable crotch portion to be removed for cleaning or replacement.

In one aspect, the present disclosure describes an undergarment having a removable crotch portion formed from one or more fabric materials, comprising: a front panel having a width extending from a first side to a second side, and also having an upper edge and a lower edge, and also having fastening means disposed at the lower edge; a rear panel having a second width extending from a first side to a second side, and also having an upper edge and a lower edge, the first and second sides of the front and rear panels joined at their respective upper edges to define a waist opening and a portion of a right leg opening and a portion of a left leg opening, the rear panel also having a lower edge with fastening means disposed on the lower edge; and a removeable crotch portion having an upper end and a lower end, the upper and lower ends including fastening means disposed thereon to engage the fastening means disposed on the lower edges of the front and rear panels such that, when fastened to the front rear panels, the removeable crotch portion defines a remaining portion of the right leg opening and a remaining portion of the left leg opening, the removable crotch portion having a pocket defined by a first layer of fabric and a second layer of fabric; and an opening in a surface of the removeable crotch portion, the opening in communication with the pocket. In one alternative aspect, the pocket formed in between the first and second layers is closed on three sides and open on one side to allow access to the pocket.

In another aspect, the pocket is held in a closed position when the removeable crotch portion is removably attached to the front and rear panels by tension applied to the removeable crotch portion when the undergarment is worn by a user.

In one aspect, the opening is disposed on an inner surface of the an inner layer of the crotch portion, and an absorbent material may be inserted into the pocket through the opening.

In yet another aspect, the fastening means includes a male snap portion and a female snap portion.

In still another aspect the fastening means includes a hook portion and a loop portion.

In another aspect, an absorbent material may be inserted into the pocket through an open side of the removeable crotch portion.

In yet another aspect, the undergarment further comprises second fastening means mounted on an edge adjacent the open side of each of the first and second layers of fabric. In one aspect the fastening means includes male and female snap portions. In another aspect the fastening means may include a hook portion and a loop portion.

In still another aspect, the undergarment may further comprise a decorative portion disposed on the waist opening defined by the upper edges of the front and rear panels.

In yet another aspect, the undergarment may further comprise a first elastic portion and a second elastic portion, the first elastic portion disposed at an edge of the right leg opening and at an edge of the left leg opening.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The following detailed description and examples are provided for the purpose of non-exhaustively describing some, but not necessarily all, examples or embodiments of the disclosed hygienic undergarment with a removable, reusable crotch portion, and shall not limit the scope of the disclosed hygienic undergarment in any way.

DETAILED DESCRIPTION OF THE PREFERRED EMBODIMENTS

The following detailed description and the accompanying drawings to which it refers are intended to describe some, but not necessarily all, examples or embodiments of the disclosed hygienic undergarment with a removable, reusable crotch portion. The described embodiments are to be considered in all respects only as illustrative and not restrictive. The contents of this detailed description and the accompanying drawings do not limit the scope of the disclosed hygienic undergarment with removable, reusable crotch portion, in any way.

Figure 1:
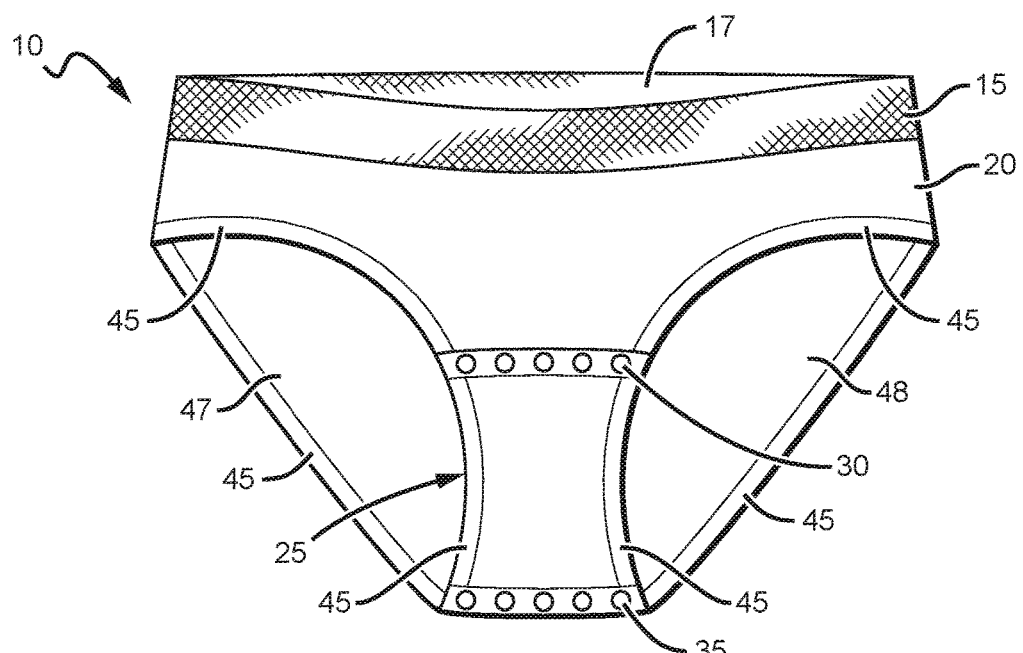
FIG. 1 is a front perspective view of an exemplary undergarment in accordance with the present disclosure.
Figure 2:
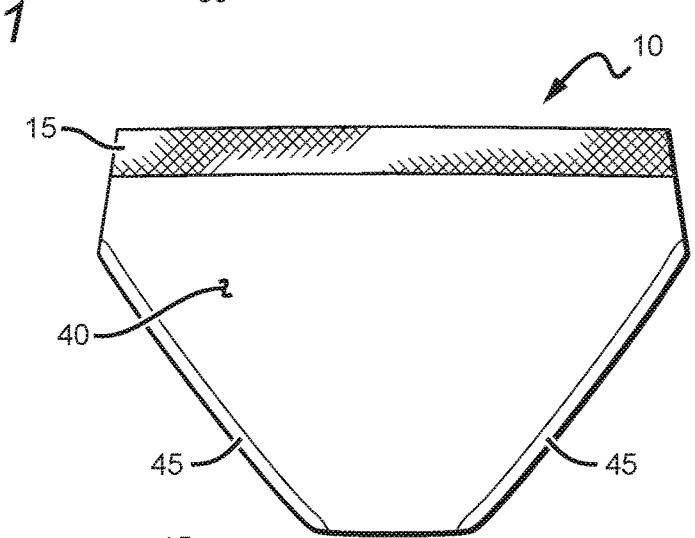
FIG. 2 is a rear perspective view of the undergarment of FIG. 1.

Referring to the drawings wherein like reference characters designate like or similar parts, FIG. 1 illustrates one exemplary embodiment of a hygienic undergarment 10 in accordance with this disclosure. Hygienic garment 10 includes a front panel 20 and a rear panel 40 (FIG. 2). Front panel 20 and rear panel 40 are connected to each other by a crotch portion 25. When the front and rear panel is assembled with the crotch portion, the assembly includes a waist encircling opening 17, and leg openings 47, 48.

Crotch portion 25 has a first end and second end, the first and second end having fastening means 30 used to fasten the first end of crotch portion 25 to the front panel 20. Similarly, fastening means 35 are used to fasten the second end of the crotch portion 25 to the rear portion 40 of the hygienic undergarment.

Also shown in capital FIGS. 1 and 2 is an optional decorative lace banding 15 that surrounds the waist opening 17 of the undergarment. FIGS. 1 and 2 also show elastic banding 45 that may be added to the hygienic undergarment surround each of leg openings 47, 48. In some embodiments, the decorative lace banding may also include an elastic component to facilitate proper fit of the undergarment at the waist of a user. Similarly, the elastic banding surrounding the leg holes assists in maintaining a proper fit of the undergarment to ensure that any leakage from a user is contained within the interior of the undergarment.

Figure 3:
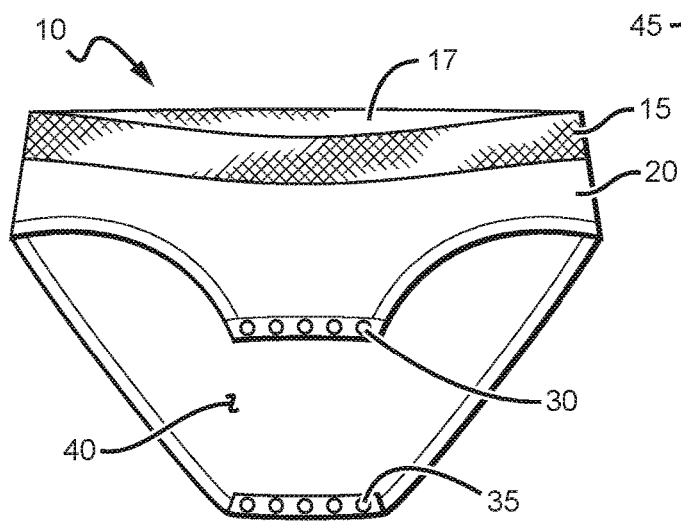
FIG. 3 is front perspective view of the undergarment of FIG. 1 where a portion of the undergarment has been removed.

FIG. 3 is front perspective view of an embodiment of the invention wherein the crotch portion 25 has been removed from the undergarment. This view also shows an exemplary location of the fastening means 30 on the front panel and fastening means 35 on the rear panel. Fastening means 30, 35 are shown in FIGS. 1-3 as being snaps. Those skilled in the art will understand that the illustrated snaps have both male and female portions. Thus, there are various combinations of the male and female portions mounted on the front and rear panels and the crotch portion.

In one example, the front panel may include female snap portions mounted on an outer surface of the front panel. In this configuration, male snap portions corresponding to the female snap portions mounted on the top surface of the front panel are mounted on an inner surface of a top end of the crotch panel. When the crotch portion is removably mounted to the front panel, the described male snap portions are engaged with the female snap portions with finger pressure so that the top end of the crotch panel is held in place upon the front panel.

Figure 7:
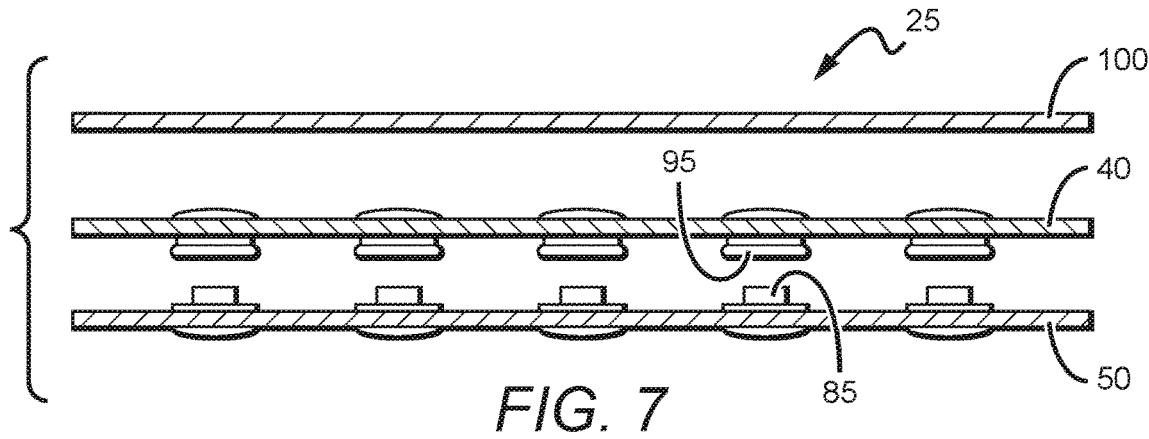
FIG. 7 is a cross-section view of one example of an end of the removable portion of FIGS. 4 and 5 showing snaps which can be used to fasten the removable portion to the remaining portion of the undergarment of FIG. 1. Also shown in an optional layer of material that can be added to hide the a visible portion of the snap from view.

Similarly, female snap portions of fastening means 35 may be mounted on an outer surface of the rear panel 40 and situated to engage male snap portions mounted on an outer surface of a bottom end of the crotch portion (See also FIG. 7). In another embodiment, where proper orientation of the crotch portion 25 in relation to the front panel 20 and rear panel 40 is important, the female snap portions may be mounted on the outer surface of the top end of the front panel so that they can be engaged with the male snap portions mounted on the inner surface of the top end of the crotch portion, as described above. In this example, however, the arrangement of male and female snap portions may be reversed at the bottom end of the crotch portion, that is, the male snap portion is mounted on the outer surface of the rear panel, and the female snap portions are mounted on the inner surface of the bottom end of the crotch panel. An advantage of this arrangement is that crotch portion will always be attached to the front and rear panels in a desired orientation.

While fastening means comprising male and female portions have been described, other types of fasteners can be utilized without departing from the scope of the intended invention. For example, instead of using male and female snap portions, fastening means such as Velcro brand fasteners (Velcro Company BVBA) may be used. Other suitable fasteners includes two sided tape, zippers, and the like.

Figure 4:
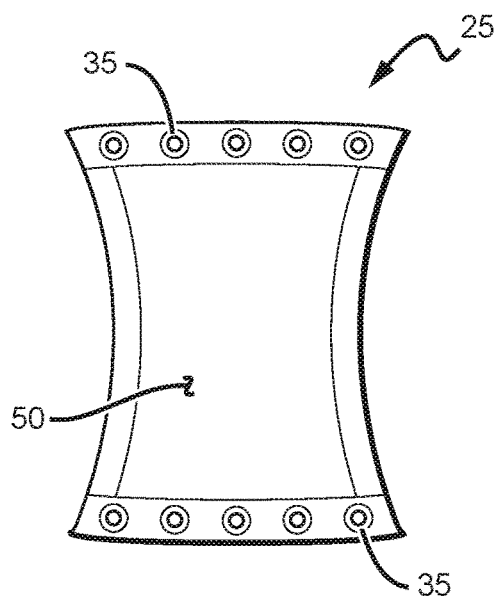
FIG. 4 is bottom view of the removed portion of the undergarment of FIG. 1.

Referring now to FIG. 4, crotch portion 25 is shown having an outer surface 50. Fastening means 30, 35 are also shown.

Figure 5:
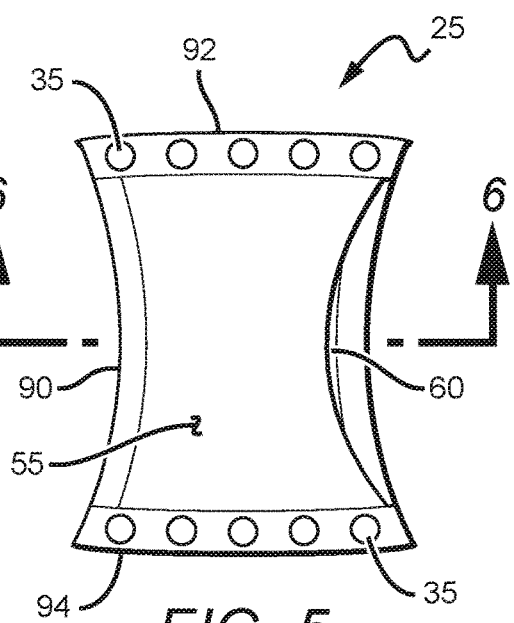
FIG. 5 is a top view of the removed portion of FIG. 4.

FIG. 5 shows the crotch portion having an inner surface 55. In this exemplary embodiment, the crotch portion is formed of at least two layers of material. The two layers are joined at a left side 90 of the crotch portion, and at the top end 92 and bottom end 94, such as, for example, by sewing or other hemming process, to form a pocket that is accessible from an opening 60 allowing access to the pocket. In use, a wearer of the undergarment may insert an absorbable pad or material into the pocket through opening 60. In one embodiment, tension is applied along a length of the crotch portion 25 when the crotch portion is appropriately attached to the front and rear panels of the undergarment, which tensions the opening in a closed position. In other embodiments, a fastening means such as snaps or Velcro may be mounted to the open edges of the opening to allow the opening to be maintained in the closed position when the fastening means are engaged.

While FIG. 5 illustrates an embodiment wherein the pocket has an opening disposed on a side of the crotch portion, the opening may be disposed in various locations along inner surface 55, that is, the surface facing the skin of the user when the undergarment is worn by the user. In such a case, the opening may take the form of a slot or slit, or be circular or non-circular in shape.

Figure 6:
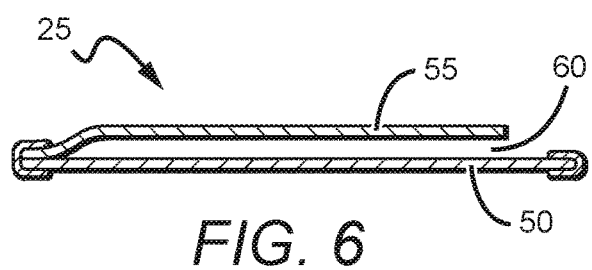
FIG. 6 is a cross-sectional view of a portion of the removed portion of the undergarment of FIGS. 4 and 5.

FIG. 6 is a cross-sectional view of the crotch portion 25 showing the arrangement of the inner surface 55, outer surface 50 and opening 60, with the pocket defined thereby in one embodiment.

FIG. 7 is a cross-section of one end of an end of the crotch portion shown being engaged with rear panel 40. In this example, male snap portions 85 are mounted on an outer surface of the end of the rear panel 40, and female snap portions 95 are mounted on the rear xsurface of the end of the crotch portion 25. As is known in the art, the female snap portion will have an outer portion that is visible on the front surface of the crotch portion. As shown in this example, an additional layer of material 100 may be added to the crotch panel to cover the visible portion of the female snap portion. This arrangement is advantageous because hiding the visible part of the female snap portion may be more aesthetically pleasing. Similarly, the visible portion of the snap at the other end of the crotch portion may also hidden in the manner described above.

Although the disclosed hygienic undergarment has been described hereabove with reference to certain examples or embodiments, various additions, deletions, alterations and modifications may be made to those described examples and embodiments without departing from the intended spirit and scope of the disclosed hygienic undergarment. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any embodiment or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims. The disclosure is limited only by the scope of the appended claims.

We claim:

1. An undergarment having a removable crotch portion, comprising:
   a front panel having a width extending from a first side to a second side, and also having an upper edge and a lower edge, and also having first fastening means disposed at the lower edge;
   a rear panel having a second width extending from a first side to a second side, and also having an upper edge and a lower edge, the first and second sides of the front and rear panels joined at their respective upper edges to define a waist opening and a portion of a right leg opening and a portion of a left leg opening, the rear panel also having a lower edge with second fastening means disposed on the lower edge;
   a removeable crotch portion having an inner surface, an outer surface, an upper end including a third fastening means and a lower end including a fourth fastening means disposed thereon to engage the first fastening means disposed on the lower edge of the front panel and the lower edge of the rear panel such that, when fastened to the front and rear panels, the removeable crotch portion defines a remaining portion of the right leg opening and a remaining portion of the left leg opening, the removeable crotch portion having a pocket defined by an inner layer of fabric configured to touch a portion of a user's skin when the undergarment is worn by the user and an outer layer of fabric, the pocket defined by three mechanically-joined closed sides and an open side, the open side defining an inner-facing opening in the inner layer of fabric, the opening further defined by one edge of an inner side of the inner layer of fabric and an inner side of the outer layer of fabric;
   an absorbent material contained within the three mechanically-joined closed sides of the pocket after the absorbent material is inserted through the open side of the pocket disposed on the inner surface of the removeable crotch portion adjacent one of the right or left leg openings.

2. The undergarment of claim 1, wherein the pocket is held in a closed position when the removeable crotch portion is removably attached to the front and rear panels by tension applied to the removeable crotch portion when the undergarment is worn by a user, the opening being longer than the upper end and longer than the lower end.

3. The undergarment of claim 1, wherein the first fastening means includes a male snap portion configured to attach to a female snap portion of the third fastening means and the second fastening means includes a female snap portion configured to attach to a male snap portion of the fourth fastening means.

4. The undergarment of claim 1, wherein the first fastening means has a hook portion configured to attach to a loop portion of the third fastening means and the second fasting means has a loop portion configured to attach to a hook portion of the fourth fastening means.

5. The undergarment of claim 1, further comprising a decorative portion disposed on the waist opening defined by the upper edges of the front and rear panels.

6. The undergarment of claim 1, further comprising a first elastic portion and a second elastic portion, the first elastic portion disposed at an edge of the right leg opening and at an edge of the left leg opening.

7. An undergarment having a removable crotch portion, comprising:
   a waist portion;
   a front panel extending from the waist portion, the front panel having a first front side, a second front side, a lower front edge between the first front side and the second front side, and a first snap disposed at the lower edge;
a rear panel extending from the waist portion, the rear panel having a first rear side, a second rear side, a lower rear edge between the first rear side and the second rear side, and a second snap disposed at the lower rear edge;
a removeable crotch portion having an inner surface, an outer surface, a first crotch side, a second crotch side, an upper end including a third snap, a lower end including a fourth snap, a pocket formed by an inner layer of fabric between the upper end and the lower end, the pocket having three mechanically-joined closed sides and an inner-facing opening;
an absorbent material contained within the pocket, the absorbent material insertable through the inner-facing opening disposed on the inner surface of the removeable crotch portion configured to touch a portion of a user's skin when the undergarment is worn by the user wherein the pocket is not accessible from the outer surface of the removeable crotch portion;
wherein the third snap removably fastens to the first snap and the fourth snap removably fastens to the second snap such that a first leg opening is formed by the first crotch side, the first front side and first rear side, and a second leg opening is formed by the second crotch side, the second front side and second rear side.

8. The undergarment of claim 7, wherein the inner-facing opening of the pocket is held in a closed position by tension applied to the removeable crotch portion when the undergarment is worn by a user, the opening being longer than the upper end and longer than the lower end.

9. The undergarment of claim 7, wherein the inner-facing opening of the pocket is longitudinal and disposed on the first crotch side.

10. The undergarment of claim 7, wherein the first front side, the second front side, the first rear side, the second rear side, the first crotch side and the second crotch side include elastic banding.

11. An undergarment having a removable crotch portion, comprising:
a waist portion;
a front panel extending from the waist portion, the front panel having a first front side, a second front side, a lower front edge between the first front side and the second front side, and a first means for fastening disposed at the lower edge;
a rear panel extending from the waist portion, the rear panel having a first rear side, a second rear side, a lower rear edge between the first rear side and the second rear side, and a second means for fastening disposed at the lower rear edge;
a removeable crotch portion having an inner surface, an outer surface, a first crotch side, a second crotch side, an upper end including a third means for fastening, a lower end including a fourth means for fastening, a pocket formed by an inner layer of fabric between the upper end and the lower end, the pocket having three mechanically-joined closed sides and an inner-facing opening;
an absorbent material contained within the pocket;
wherein the third means for fastening removably fastens to the first fastening means and the fourth means for fastening removably fastens to the second means for fastening such that a first leg opening is formed by the first crotch side, the first front side and first rear side, and a second leg opening is formed by the second crotch side, the second front side and second rear side.

12. The undergarment of claim 11, wherein the inner-facing opening of the pocket is held in a closed position by tension applied to the removeable crotch portion when the undergarment is worn by a user, the opening being longer than the upper end and longer than the lower end.

13. The undergarment of claim 11, wherein the inner-facing opening of the pocket is longitudinal and disposed on the first crotch side.

14. The undergarment of claim 11, wherein the absorbent material is insertable through the inner-facing opening disposed on the inner surface of the removeable crotch portion configured to touch a portion of a user's skin when the undergarment is worn by the user wherein the pocket is not accessible from the outer surface of the removeable crotch portion.

15. The undergarment of claim 11, wherein the first front side, the second front side, the first rear side, the second rear side, the first crotch side and the second crotch side include elastic banding.

16. The undergarment of claim 11, wherein the first means for fastening, the second means for fastening, the third means for fastening and the fourth means for fastening are snaps.

17. An undergarment having a removable crotch portion, comprising:
a front panel having a width extending from a first side to a second side, and also having an upper edge and a lower edge, and also having first fastening means disposed at the lower edge;
a rear panel having a second width extending from a first side to a second side, and also having an upper edge and a lower edge, the first and second sides of the front and rear panels joined at their respective upper edges to define a waist opening and a portion of a right leg opening and a portion of a left leg opening, the rear panel also having a lower edge with second fastening means disposed on the lower edge;
a removeable crotch portion having an inner surface, an outer surface, an upper end including a third fastening means and a lower end including a fourth fastening means disposed thereon to engage the first fastening means disposed on the lower edge of the front panel and the lower edge of the rear panel such that, when fastened to the front and rear panels, the removeable crotch portion defines a remaining portion of the right leg opening and a remaining portion of the left leg opening, the removeable crotch portion having a pocket defined by an inner layer of fabric configured to touch a portion of a user's skin when the undergarment is worn by the user and an outer layer of fabric, the pocket defined by three mechanically-joined closed sides and an open side, the open side defining an inner-facing opening in the inner layer of fabric, the opening further defined by one edge of an inner side of the inner layer of fabric and an inner side of the outer layer of fabric;
an absorbent material inserted into the pocket through the opening disposed on the inner surface of the removeable crotch portion wherein the pocket is not accessible from the outer surface of the removeable crotch portion.

18. The undergarment of claim 17, wherein the pocket is held in a closed position when the removeable crotch portion is attached to the front and rear panels by tension applied to the removeable crotch portion when the undergarment is worn by a user, the opening being longer than the upper end and longer than the lower end.

19. The undergarment of claim 17, wherein the first fastening means includes a male snap portion configured to attach to a female snap portion of the third fastening means and the second fastening means includes a female snap portion configured to attach to a male snap portion of the fourth fastening means.

20. The undergarment of claim 17, further comprising a first elastic portion and a second elastic portion, the first elastic portion disposed at an edge of the right leg opening and at an edge of the left leg opening.

* * * * *